United States Patent
Gao et al.

(10) Patent No.: US 9,585,626 B2
(45) Date of Patent: Mar. 7, 2017

(54) METHODS AND SYSTEMS FOR SPECTRAL CT IMAGING

(71) Applicant: General Electric Company, Schenectady, NY (US)

(72) Inventors: Hewei Gao, Pewaukee, WI (US); Tonghe Wang, Atlanta, GA (US); Jiahua Fan, New Berlin, WI (US); Guangzhi Cao, Madison, WI (US)

(73) Assignee: General Electric Company, Schenectady, NY (US)

( * ) Notice: Subject to any disclaimer, the term of this patent is extended or adjusted under 35 U.S.C. 154(b) by 76 days.

(21) Appl. No.: 14/567,828

(22) Filed: Dec. 11, 2014

(65) Prior Publication Data

US 2016/0166221 A1 Jun. 16, 2016

(51) Int. Cl.
*A61B 1/00* (2006.01)
*A61B 6/00* (2006.01)
*G06T 11/00* (2006.01)
*A61B 6/03* (2006.01)

(52) U.S. Cl.
CPC .............. *A61B 6/482* (2013.01); *A61B 6/032* (2013.01); *A61B 6/52* (2013.01); *G06T 11/005* (2013.01); *G06T 11/006* (2013.01); *G06T 2211/408* (2013.01)

(58) Field of Classification Search
None
See application file for complete search history.

(56) References Cited

U.S. PATENT DOCUMENTS

| 8,165,264 B2 | 4/2012 | Zou | |
| 8,290,232 B2* | 10/2012 | Liu | A61B 6/032 382/131 |
| 8,363,917 B2* | 1/2013 | Fan | G06T 11/008 378/4 |
| 2004/0264627 A1* | 12/2004 | Besson | A61B 6/508 378/5 |
| 2009/0052612 A1* | 2/2009 | Wu | A61B 6/032 378/5 |
| 2010/0215233 A1 | 8/2010 | Hsieh | |

(Continued)

FOREIGN PATENT DOCUMENTS

WO  2013165396 A1  11/2013

OTHER PUBLICATIONS

Lifeng Yu et al, "Pre-Reconstruction Three-Material Decomposition in Dual-Energy CT", Proceedings of Spie, vol. 7258, Feb. 26, 2009, pp. 72583V-72583V-8.

(Continued)

*Primary Examiner* — Kim Vu
*Assistant Examiner* — Molly Delaney
(74) *Attorney, Agent, or Firm* — John D. Russell

(57) ABSTRACT

Various methods and systems for dual energy spectral computed tomography imaging are provided. In one embodiment, a method for dual energy imaging comprises generating an image from a higher energy dataset and an updated lower energy dataset, wherein the updated lower energy dataset comprises a combination of a lower energy dataset and a pseudo projection dataset generated from the higher energy dataset. In this way, a weak low energy signal may be recovered, thereby enabling image reconstruction in spite of photon starvation and sparse views.

19 Claims, 4 Drawing Sheets

(56) References Cited

U.S. PATENT DOCUMENTS

| | | | | |
|---|---|---|---|---|
| 2011/0085719 | A1* | 4/2011 | Fan | G06T 11/008 382/131 |
| 2011/0282181 | A1* | 11/2011 | Wang | A61B 5/0095 600/407 |
| 2012/0236987 | A1* | 9/2012 | Ruimi | A61B 6/032 378/19 |
| 2013/0053689 | A1* | 2/2013 | Das | A61B 6/03 600/425 |
| 2013/0308745 | A1* | 11/2013 | Goshen | G06T 11/005 378/5 |
| 2014/0005533 | A1* | 1/2014 | Grasruck | A61B 6/032 600/425 |
| 2014/0010427 | A1* | 1/2014 | Kriston | A61B 6/12 382/131 |
| 2015/0182176 | A1* | 7/2015 | Jin | A61B 6/4241 378/5 |

OTHER PUBLICATIONS

Li Yuanji et al., "Towards dose reduction for dual-energy CT: A non-local image improvement method and its application"., Nuclear Instruments & Methods in Physics Research. Sectio A: Accelerators, Specrometers, Detectors, and Associated Equipment, Elsevier BV *North-Holland, NL, vol. 770, Oct. 23, 2014, pp. 211-217.
International Search Report and Written Opinion from Corresponding PCT application PCT/US2015/050864 dated Dec. 16, 2015; 13 pages.

\* cited by examiner

METHODS AND SYSTEMS FOR SPECTRAL CT IMAGING

FIELD

Embodiments of the subject matter disclosed herein relate to diagnostic imaging, and more particularly, to image reconstruction for dual energy spectral imaging.

BACKGROUND

Dual or multi-energy spectral computed tomography (CT) systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

However, in some cases the detected signals may not provide sufficient information to resolve the energy dependence of the material being imaged due to low photon flux, or photon starvation, when the attenuated x-ray beam at the detectors is weak. For example, photon starvation may occur for low energy x-ray beams due to a reduced number of photons generated compared to high energy x-ray beams. As a result, low energy data may be noisier and less reliable than high energy data, which may in turn cause substantial artifacts in an image reconstructed from the data. This problem with low energy data may be further exacerbated by sparse view data acquisition, where data is acquired at fewer views and therefore there is less low energy data overall.

BRIEF DESCRIPTION

In one embodiment, a method for dual energy imaging comprises generating an image from a higher energy dataset and an updated lower energy dataset, wherein the updated lower energy dataset comprises a combination of a lower energy dataset and a pseudo projection dataset generated from the higher energy dataset. In this way, a weak low energy signal may be recovered, thereby enabling image reconstruction in spite of photon starvation and sparse views.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of image reconstruction for dual energy spectral imaging. In particular, methods and systems for low energy signal recovery are disclosed. The operating environment of the present invention is described with respect to a sixty-four-slice computed tomography (CT) system, such as the CT imaging system shown in FIGS. 1 and 2. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic radiation. The invention will be described with respect to a "third generation" CT scanner, but is equally applicable with other CT systems.

Figure 1:
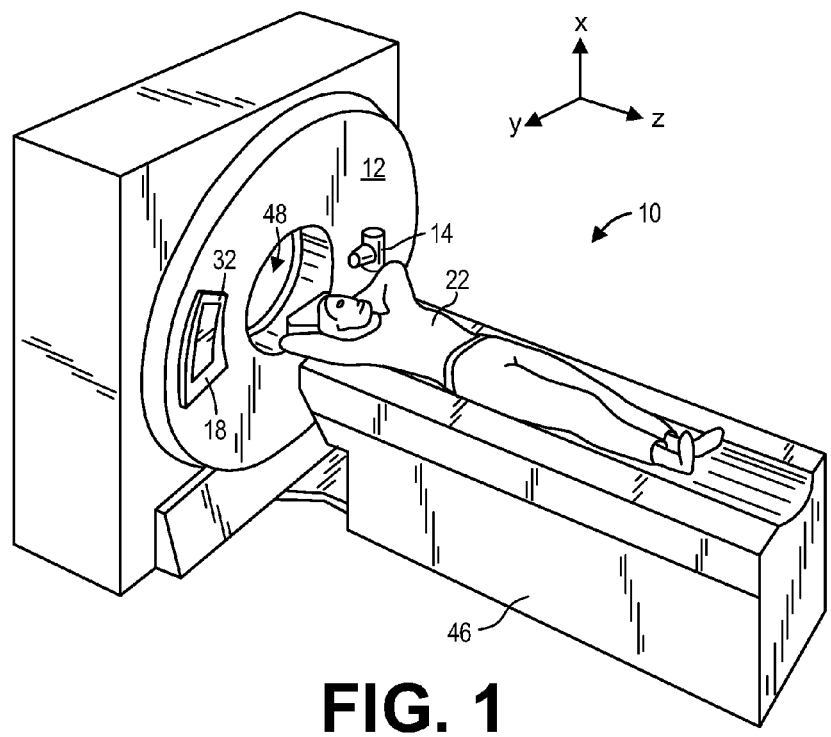
FIG. 1 is a pictorial view of an imaging system according to an embodiment of the invention.
Figure 2:
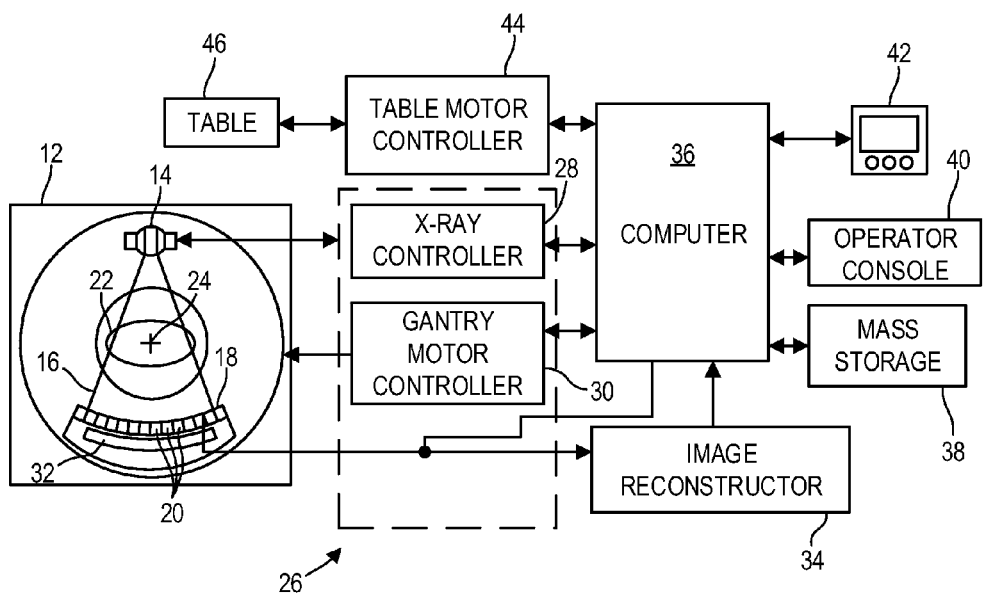
FIG. 2 is a block schematic diagram of an exemplary imaging system according to an embodiment of the invention.

Referring to FIGS. 1 and 2, a CT imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Detector assembly 18 is formed by a plurality of detectors 20 and data acquisition system (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 and gantry 12. Particularly, table 46 moves patient 22 through a gantry opening 48 of FIG. 1 in whole or in part.

Each detector 20 may be designed to directly convert radiographic energy to electrical signals containing energy discriminatory or photon count data. Thus, in one embodiment, each detector 20 includes a semiconductor layer fabricated from CZT. Each detector 20 also includes a plurality of metallized anodes attached to the semiconductor layer. Such detectors 20 may include an electrical circuit having multiple comparators thereon which may reduce statistical error due to pileup of multiple energy events.

A discussion is now presented in connection with a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. Regarding terminology, a set of projection data obtained at a higher tube kVp level may be interchangeably referred to herein as a high kVp dataset or a high energy dataset, while a set of projection data obtained at a lower tube kVp level may be interchangeably referred to herein as a low kVp dataset or a low energy dataset.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, a compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it needs not be an integer. This effective Z representation property stems from a well-known fact that x-ray attenuation in the energy range useful for diagnostic x-ray imaging is strongly related to the electron density of compounds, which is also related to the atomic number of materials.

The basis for the present disclosure is the fact that the same object 22 is scanned at both high and low energies. For dual energy data acquisition, typically a low density material and a high density material, such as water and iodine, are chosen as two basis materials. The material density for water is dominated by projection data acquired at high energies while the material density for iodine is dominated by projection data acquired at low energies. However, an acquired high energy dataset may still contain data regarding a high density material such as iodine in addition to data regarding a low-density material such as water. Therefore, as described further herein, data regarding the high-density material in the high energy dataset may be used to compensate for a low signal strength of the low energy dataset. Such an approach may substantially improve images generated using dual energy imaging techniques, especially for instances of low photon flux of low energy photons.

In some examples, CT system 10 may be configured for sparse view data acquisition and image reconstruction. In such examples, the x-ray source 14 and the detector array 18 may be configured to acquire data at a reduced number of views compared to a typical scan, thereby reducing a radiation dosage. The various approaches described further herein for recovering a low energy signal may enable a sparse view configuration for dual or multi-energy spectral CT imaging. For example, a dearth of low energy data due to photon starvation and/or sparse view data acquisition may be compensated using information from high energy data.

Figure 3:
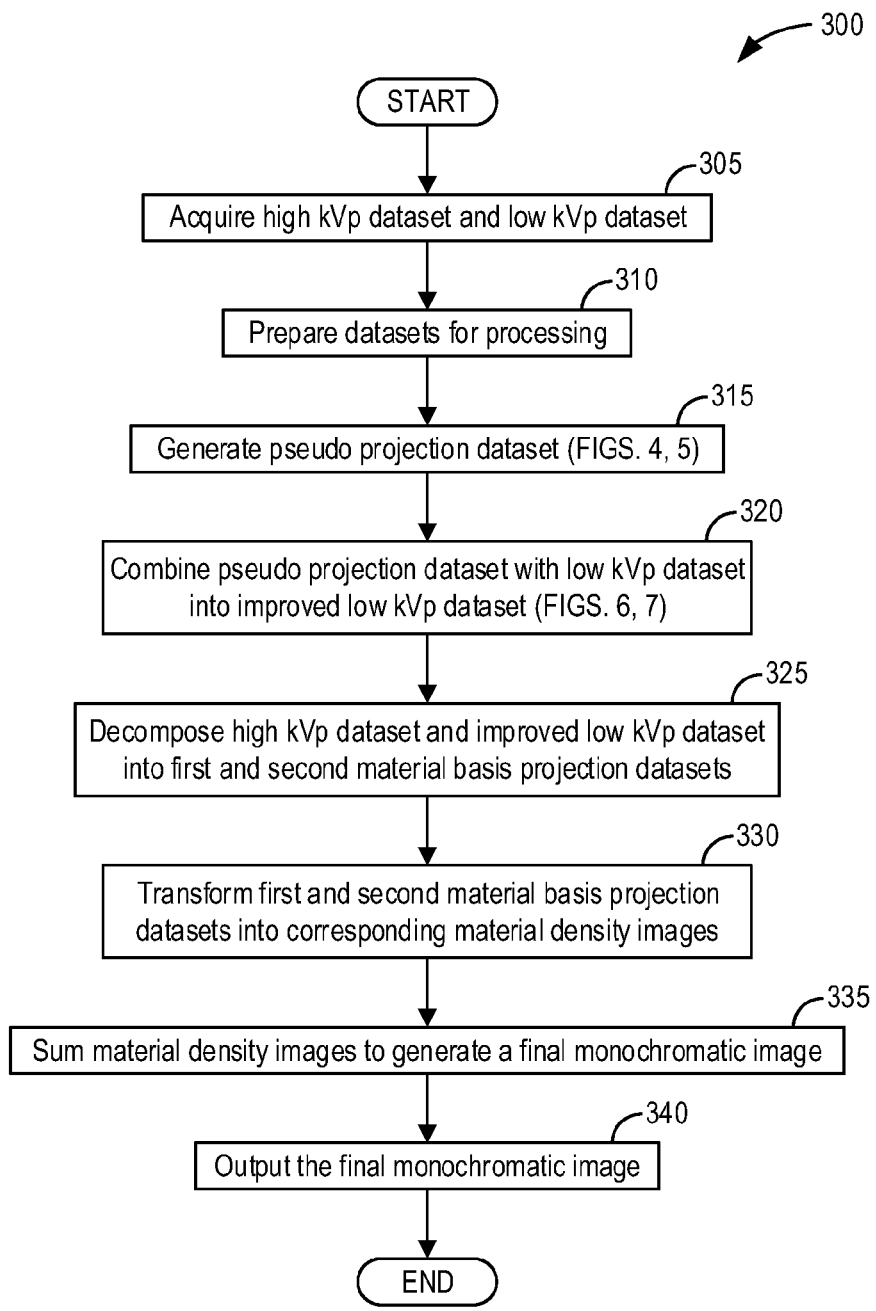
FIG. 3 is a high-level flow chart illustrating an example method for low-energy signal recovery according to an embodiment of the invention.

FIG. 3 is a high-level flow chart illustrating an example method 300 for low-energy signal recovery according to an embodiment of the invention. In particular, method 300 relates to generating a monochromatic image from material density images, where the material density images are based on a higher energy dataset and an updated lower energy dataset. As described further herein, the updated lower energy dataset may include lower energy data recovered using the higher energy dataset. In this way, low photon flux for low energy data acquisition may be compensated. As a result, an image quality of a CT image may be improved for CT imaging systems subject to photon starvation or that are configured for sparse view data acquisition. Method 300 may be described with reference to the system and components shown in FIGS. 1 and 2, however the method may be applied to other systems without departing from the scope of the present disclosure.

Method 300 may begin at 305. At 305, method 300 may include acquiring a high kVp dataset and a low kVp dataset. The higher energy dataset and the lower energy dataset may be acquired using any dual energy technology, including but not limited to fast kV switching, two-tube two-detector (2T2D), dual layer, rotate-rotate (rot-rot), photon counting, and so on. After acquiring the datasets, method 300 may continue to 310.

At 310, method 300 may include preparing the higher and lower kVp datasets for processing. Preparing the higher and lower kVp datasets for processing may comprise, for example, time-aligning the views, interpolating missing data, applying gain normalization, applying data corrections for detector artifacts, and so on. After preparing the datasets for processing, method 300 may continue to 315.

At 315, method 300 may include generating a pseudo projection dataset. In one example, generating a pseudo projection dataset may comprise reconstructing an intermediate image from the higher kVp dataset or a combination of the higher kVp dataset and the lower kVp dataset, characterizing a high-density material in the intermediate image, and forward projecting the high-density material in the intermediate image. The projection dataset produced by the forward projection may comprise the pseudo projection dataset. A method for generating a pseudo projection dataset using intermediate image reconstructions and forward projection is described further herein with regard to FIG. 4.

In another example, generating a pseudo projection dataset may comprise generating a pseudo projection dataset directly from the higher kVp dataset. In particular, by assuming that all material in the scanned object is a single material, generating the pseudo projection dataset directly from the higher kVp dataset may comprise scaling the high kVp dataset by a ratio of an attenuation coefficient of the single material at lower energies to an attenuation coefficient of the single material at higher energies. The single material may be selected, for example, by a user. In one example, the single material selected may comprise water. Selecting water as the single material comprises assuming that all material in the scanned object is water-equivalent for the human body. In other examples, a single material other than water may be selected, for example when imaging a non-human object such as luggage. A method for generating a pseudo projection dataset directly from a higher kVp dataset is described further herein with regard to FIG. 5.

At 320, method 300 may include combining the pseudo projection dataset with the measured lower kVp dataset into an updated lower kVp dataset. In one example, the updated lower kVp dataset may comprise a weighted combination of the pseudo projection dataset and the measured lower kVp dataset. Such a method for combining the pseudo projection dataset and the measured lower kVp dataset is described further herein with regard to FIG. 6. In another example, the pseudo projection dataset and the measured lower kVp dataset may be combined using regularization-based iterative optimization. Such a method for combining the pseudo projection dataset and the measured low kVp dataset is described further herein with regard to FIG. 7.

After generating the updated lower kVp dataset, method 300 may continue to 325. At 325, method 300 may include decomposing the higher kVp dataset and the updated lower kVp dataset into first and second material basis projection datasets. Decomposition may be performed using, for example, basis material decomposition (BMD) wherein the measured projections are converted to a set of density line-integral projections as described herein above and known in the art. The material bases may comprise, for example, a water basis and an iodine basis. In other examples, the material bases may comprise different combinations of materials.

At 330, method 300 may include transforming the first and second material basis projection datasets into corresponding material density images. Transforming the datasets into corresponding density images may comprise applying an image reconstruction algorithm, such as filtered back projection, to the datasets to transform the data from projection space to image space.

At 335, method 300 may include summing the material density images to generate a final monochromatic image. At 340, method 300 may include outputting the final monochromatic image. The monochromatic image may be output to memory for later retrieval. As another example, the monochromatic image may be output to a display device for display to a user. Method 300 may then end.

Figure 4:
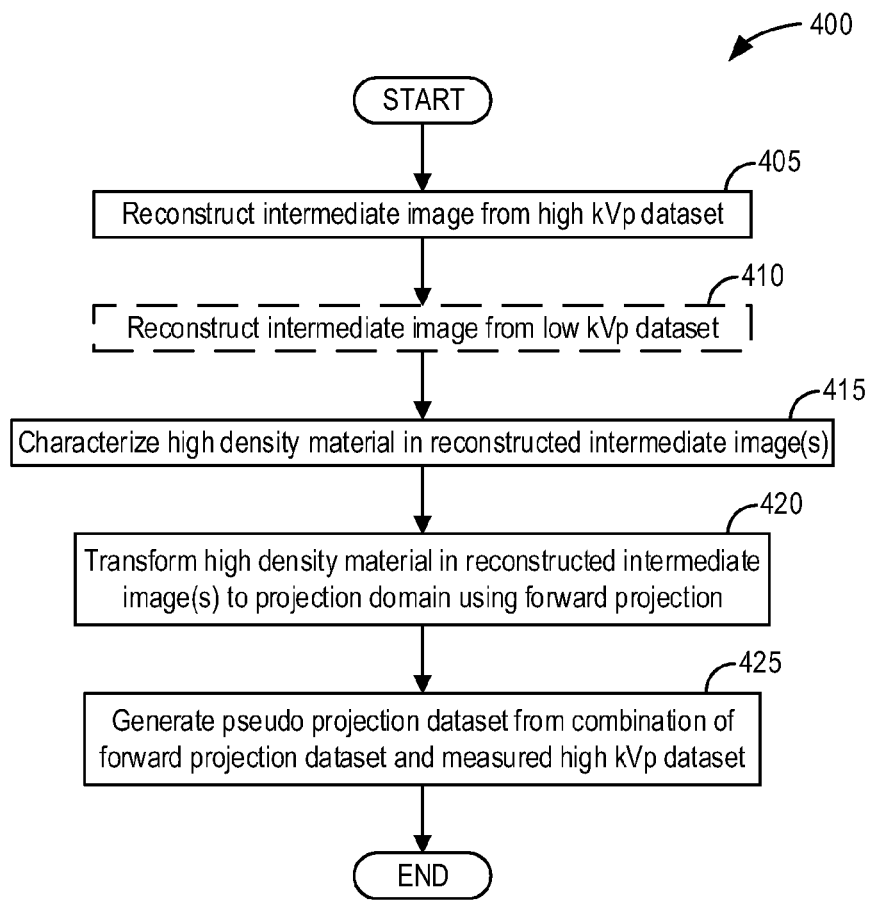
FIG. 4 is a high-level flow chart illustrating an example method for synthesizing low-energy projection data from high-energy projection data according to an embodiment of the invention.

FIG. 4 is a high-level flow chart illustrating an example method 400 for synthesizing low-energy projection data from high-energy projection data according to an embodiment of the invention. In particular, method 400 relates to generating a pseudo projection dataset using image reconstruction and forward projection. Furthermore, method 400 may function as a subroutine of method 300 shown in FIG. 3. Specifically, method 400 may comprise the step 315 of generating a pseudo projection dataset. Method 400 may be described with reference to the system and components shown in FIGS. 1 and 2, however it should be understood that the method may be applied to other systems with departing from the scope of the current disclosure.

Method 400 may begin at 405. At 405, method 400 may include reconstructing an intermediate image from the higher kVp dataset. The intermediate image may be reconstructed using any suitable image reconstruction algorithm, including but not limited to forward back projection.

At 410, method 400 may optionally include reconstructing an intermediate image from the lower kVp dataset. The intermediate image may be reconstructed using any suitable image reconstruction algorithm, including but not limited to forward back projection. Such an intermediate image may provide additional accuracy in subsequent steps, however method 400 may sufficiently generate a pseudo projection dataset as described herein without the inclusion of step 410.

Continuing at 415, method 400 may include characterizing the high-density material in the reconstructed intermediate images. In examples where step 410 is not performed, only the intermediate image reconstructed from the higher kVp dataset at 405 may be utilized for material characterization. In examples where step 410 is performed, both the intermediate image reconstructed from the higher kVp dataset at 405 and the intermediate image reconstructed from the lower kVp dataset at 410 may be utilized for material characterization. The high-density material may be characterized, for example, using material segmentation. Additionally or alternatively, material decomposition may be applied to the intermediate images to estimate high-density materials.

At 420, method 400 may include transforming the high-density material in the reconstructed images to the projection domain using forward projection, thereby yielding a forward projection dataset containing the high-density material.

At 425, method 400 may include generating a pseudo projection dataset from a combination of the forward projection dataset and the measured higher kVp dataset. As a non-limiting example, high energy projection data $P_h$ may be modeled as a function of a thickness of water $L_w$ and a thickness of iodine $L_{io}$:

$$P_h(L_w, L_{io}) = -\ln\left(\frac{\int S_h(E)\exp[-(\mu_w(E)L_w + \mu_{io}L_{io})]dE}{\int S_h(E)dE}\right),$$

where $S_h(E)$ is a high energy spectra as a function of energy E, $\mu_w(E)$ is an attenuation coefficient of water as a function of energy, and $\mu_{io}$ is an attenuation coefficient of iodine. Similarly, low energy projection data $P_l$ may be modeled as above by replacing the high energy spectra $S_h(E)$ with low energy spectra $S_l(E)$. The effective iodine projection after water attenuation may therefore be computed as:

$$P_{io}(L_w, L_{io}) = P_h(L_w, L_{io}) - P_h(L_w, 0).$$

The iodine projection $P_{io}$ and the high energy projection $P_h$ may then be used to calculate the low energy projection $P_l$:

$$P_l = \Sigma_{i,j}^{N,M} \alpha_{ij} P_h^i P_{io}^j,$$

where $\alpha$ comprises coefficients determined from system calibration. In some examples, the polynomial system coefficients $\alpha$ may be computed using simulated data and the above expression.

With the relation described above between the low energy projection data and the high energy projection data in mind, a pseudo projection dataset $P_{pp}$ may be computed using:

$$P_{pp} \approx \Sigma_{i,j}^{N,M} \alpha_{ij} P_h^i P_{fwd}^j,$$

where $P_{fwd}$ comprises the forward projection dataset computed at 420. Note that the forward projection dataset comprises an effective iodine projection as discussed above.

Therefore, generating the pseudo projection dataset based on a combination of the forward projection dataset and the measured higher kVp dataset may comprise inputting the forward projection dataset and the higher kVp dataset into the polynomial approximation for the pseudo projection set $P_{pp}$ given above. After generating the pseudo projection dataset, method 400 may then end. The pseudo projection dataset may then be used as described herein above with regard to FIG. 3.

While method 400 provides a robust approach for generating a pseudo projection dataset, the process of reconstructing intermediate images, characterizing the high-density material, and forward projecting the intermediate images may increase computational expense of the total CT imaging workflow. As described herein with regard to FIG. 5, a first-order approximation to method 400 may provide a pseudo projection dataset with a minimal increase in computational resources and time.

Figure 5:
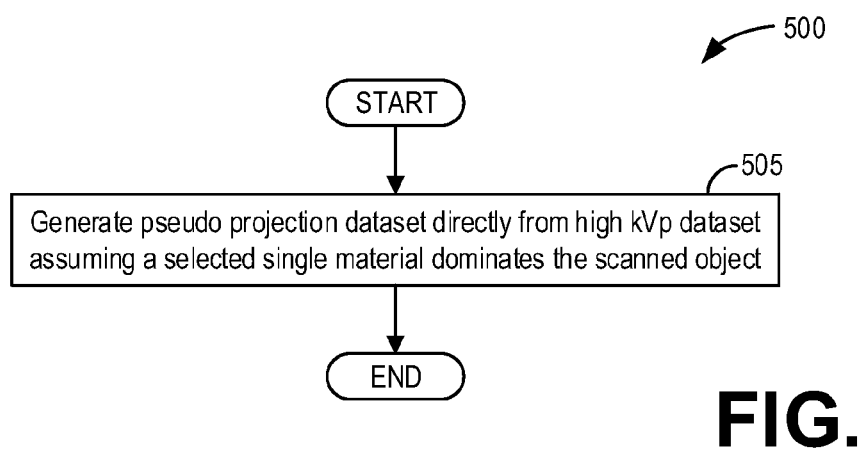
FIG. 5 is a high-level flow chart illustrating an example method for synthesizing low-energy projection data directly from high-energy projection data according to an embodiment of the invention.

FIG. 5 is a high-level flow chart illustrating an example method 500 for synthesizing low-energy projection data directly from high-energy projection data according to an embodiment of the invention. Method 500 may function as a subroutine of method 300 shown in FIG. 3. Specifically, method 500 may comprise the step 315 of generating a pseudo projection dataset. Method 500 may be described with reference to the system and components shown in FIGS. 1 and 2, however it should be understood that the method may be applied to other systems with departing from the scope of the current disclosure.

Method 500 may begin at 505. At 505, method 500 may include generating a pseudo projection dataset directly from the higher kVp dataset. For example, the pseudo projection dataset may be generated directly from the higher kVp dataset by assuming that all material in the imaged subject is a single material. The choice of the single material may, for example, be selected by a user. In some examples, there may be a default selection for the single material. For example, a default selection may comprise water, and so the pseudo projection dataset may be generated directly from the higher kVp dataset by assuming that all material in the imaged subject is water-equivalent, or that the scanned object only contains water. Such an assumption is reasonable given that a human body predominantly comprises water. Furthermore, the ratio of photon flux through a depth of a material at low energy to the photon flux at high energy through the same depth of the same material is roughly constant regardless of the material or the depth of the material. With this in mind, a pseudo projection dataset may be generated by:

$$P_{pp} = P_h \times \frac{\mu_w(E_{eff}^{low})}{\mu_w(E_{eff}^{high})},$$

where the numerator comprises the attenuation of the dominating material in the scanning object (e.g., water for human body) at an effective high energy and the denominator comprises the attenuation of the dominating material at an effective low energy. In other words, the pseudo projection dataset may be generated by scaling the higher energy dataset with a ratio of an attenuation coefficient of the selected material (e.g., water for human body) at low and high energies. Method 500 may then end.

Figure 6:
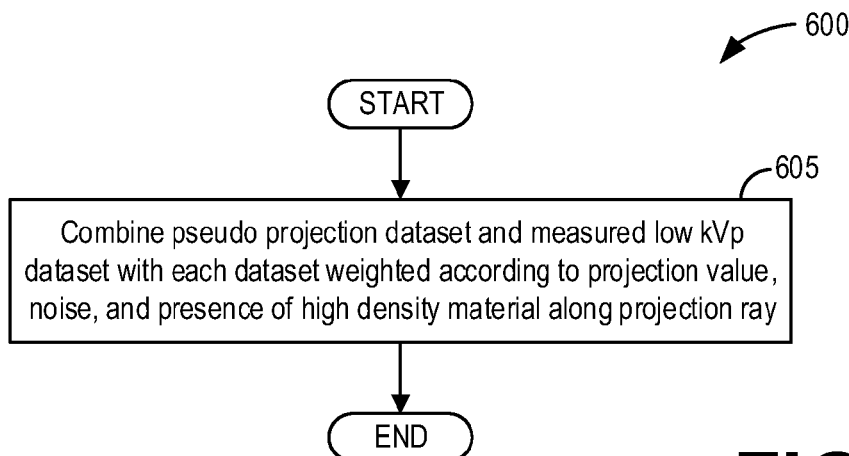
FIG. 6 is a high-level flow chart illustrating an example method for weighting synthesized and measured low-energy projection data according to an embodiment of the invention.

FIG. 6 is a high-level flow chart illustrating an example method for weighting synthesized and measured low-energy projection data according to an embodiment of the invention. Method 600 may function as a subroutine of method 300 shown in FIG. 3. Specifically, method 600 may comprise the step 320 of combining a pseudo projection dataset with a lower kVp dataset into an updated lower kVp dataset. Method 600 may be described with reference to the system and components shown in FIGS. 1 and 2, however it should be understood that the method may be applied to other systems with departing from the scope of the current disclosure.

Method 600 may begin at 605. At 605, method 600 may include combining the pseudo projection dataset and the measured lower kVp dataset. Each dataset may be weighted according to projection value, noise, and presence of high-density material along a projection ray. For example, an updated lower kVp dataset P' may be generated from the pseudo projection dataset $P_{pp}$, and the original lower kVp data set $P_{orig}$ using:

$$P' = wP_{pp} + (1-w)P_{orig},$$

with the weight w defined as:

$$w = \frac{1}{e^{\frac{P_{orig}-T}{K}}+1} \times g(P_{io}),$$

where T is a threshold, K is a constant window, and the function $g(P_{io})$ may be designed to give more weight to the pseudo low kV data when more high-density materials are in the entire projection ray. For example, the function $g(P_{io})$ may be defined as:

$$g(P_{io}) = \begin{cases} \frac{P_{io}}{P_T}, & \text{for } P_{io} < P_T, \\ 1, & \text{otherwise} \end{cases}$$

where $P_T$ comprises a threshold. As the quantity of iodine in a projection ray increases towards the threshold $P_T$, the weight given to the pseudo projection data increases. When the quantity of iodine in a projection ray is greater than or equal to the threshold PT, substantially more weight is given to the pseudo projection data due to the (1−w) dependence of the original projection data on the weighting function. Method 600 may then end.

Figure 7:
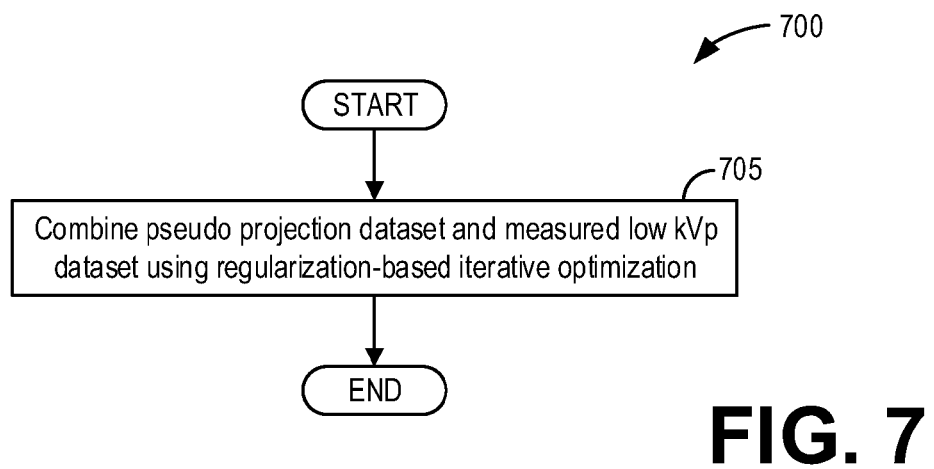
FIG. 7 is a high-level flow chart illustrating an example method for combining synthesized and measured low-energy projection data with regularization-based iterative optimization according to an embodiment of the invention.

FIG. 7 is a high-level flow chart illustrating an example method 700 for combining synthesized and measured low-energy projection data with regularization-based iterative optimization according to an embodiment of the invention. Method 700 may function as a subroutine of method 300 shown in FIG. 3. Specifically, method 700 may comprise the step 320 of combining a pseudo projection dataset with a lower kVp dataset into an updated lower kVp dataset. Method 700 may be described with reference to the system and components shown in FIGS. 1 and 2, however it should be understood that the method may be applied to other systems with departing from the scope of the current disclosure.

Method 700 may begin at 705. At 705, method 700 may include combining the pseudo projection dataset and the measured lower kVp dataset. The pseudo projection dataset and the measured lower kVp dataset may be combined using regularization-based iterative optimization. In particular, an updated lower kVp dataset may be obtained using a minimization function that includes an L2 regularization given by:

$$\vec{P} = \operatorname{argmin}\left[\frac{1}{\rho(\vec{P}, \vec{P}_{pp})^2} + \frac{\lambda}{2}\|\vec{P} - \vec{P}_{orig}\|_2\right],$$

where the linear coefficient ρ is defined using variances σ:

$$\rho = \frac{\sigma_{PP_{pp}}}{\sigma_P \sigma_{P_{pp}}} = \frac{(\vec{P} - \mu \vec{i})^T (\vec{P}_{pp} - \mu' \vec{i})}{\sqrt{(\vec{P} - \mu \vec{i})^T (\vec{P}_{pp} - \mu \vec{i})}\sqrt{(\vec{P} - \mu' \vec{i})^T (\vec{P}_{pp} - \mu' \vec{i})}},$$

the term μ comprises a mean of $\vec{P}$, the term μ' comprises a mean of $\vec{P}_{pp}$, and λ comprises a penalty weighting factor that determines the importance of data fidelity of the measured projection. Method 700 may then end.

The technical effect of the disclosure may include the compensation for photon starvation in low energy CT data acquisition. Another technical effect of the disclosure may include an improved image quality of images generated by a dual energy CT imaging system without increasing a radiation dosing. For example, the compensation for photon starvation may reduce the presence of shading artifacts, bias artifacts, and so on in a reconstructed image. Yet another technical effect of the disclosure may include an improved image quality of images generated from data acquired with a sparse view configuration of a CT imaging system.

In one embodiment, a method for dual energy imaging comprises generating an image from a higher energy dataset and an updated lower energy dataset. The updated lower energy dataset comprises a combination of a lower energy dataset and a pseudo projection dataset generated from the higher energy dataset.

In one example, generating the pseudo projection dataset from the higher energy dataset comprises reconstructing an intermediate image from the higher energy dataset, characterizing a high-density material in the intermediate image, generating a forward projection dataset based on the high-density material in the intermediate image, and combining the forward projection dataset and the higher energy dataset into the pseudo projection dataset. In one example, generating the pseudo projection dataset from the higher energy dataset further comprises reconstructing a second intermediate image from the lower energy dataset. In such an example, generating the forward projection dataset is further based on a characterization of the high-density material in the second intermediate image. In some examples, the intermediate image is reconstructed using filtered back projection.

In another example, the pseudo projection dataset is generated directly from the higher energy dataset by scaling the higher energy dataset with a ratio of an attenuation coefficient of a selected material at low and high energies. In one example, the selected material comprises water (e.g., when imaging a human body).

In yet another example, the combination of the lower energy dataset and the pseudo projection dataset comprises a weighted sum of the lower energy dataset and the pseudo projection dataset. Alternatively, the lower energy dataset and the pseudo projection dataset are combined using a regularization-based iterative optimization.

In one example, generating the image from the higher energy dataset and the updated lower energy dataset comprises decomposing the high energy dataset and the updated lower energy datasets into material basis datasets, transforming the material basis datasets into corresponding material density images, and summing the material density images to produce the image.

In another embodiment, a method for dual energy imaging comprises acquiring a higher energy dataset and a lower energy dataset, generating a pseudo projection dataset directly from the higher energy dataset, generating an updated lower energy dataset based on a weighted combination of the lower energy dataset and the pseudo projection dataset, and generating an image based on the higher energy dataset and the updated lower energy dataset.

In one example, generating the pseudo projection dataset directly from the higher energy dataset comprises scaling the higher energy dataset with a ratio of an attenuation coefficient of a selected material at lower and higher energies. For example, the selected material may comprise water for a human body. As another example, the weighted combination applies a larger weight to the pseudo projection dataset when a high-density material is in a projection ray.

In one example, generating the image comprises decomposing the higher energy dataset and the updated lower energy dataset into material basis datasets, transforming the material basis datasets into material density images, summing the material density images, and outputting the summed material density images to a display. In one example, the material bases of the material basis datasets comprise iodine and water. As another example, the transformation comprises a filtered back projection.

In yet another embodiment, an imaging system, comprises: an x-ray source that emits a beam of x-rays toward an object to be imaged, the x-ray source configured to emit x-rays with a higher energy and a lower energy; a detector that receives the x-rays attenuated by the object; a data acquisition system (DAS) operably connected to the detector. The system further comprises a computer operably connected to the DAS and programmed with instructions in non-transitory memory that when executed cause the computer to generate pseudo projection data based on higher energy data received from the DAS and generate an image based on the higher energy data and the pseudo projection data.

In one example, the computer is further programmed with instructions in non-transitory memory that when executed cause the computer to combine the pseudo projection data with lower energy data received from the DAS, decompose the combined data and the higher energy data into material basis datasets, and transform the material basis datasets into material density images. In such an example, generating the image comprises summing the material density images.

In another example, the computer is further programmed with instructions in non-transitory memory that when executed cause the computer to decompose the pseudo projection data and the higher energy data into material basis datasets, transform the material basis datasets into material density images, and sum the material density images to generate the image.

In one example, the detector and the x-ray source are configured to acquire data in a sparse view mode. In another example, the x-ray source is configured to switch between a high peak kilovoltage and a low peak kilovoltage to generate respectively the higher energy data and lower energy data.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for dual energy imaging, comprising:
   acquiring a higher energy dataset and a lower energy dataset;
   generating a pseudo projection dataset from the higher energy dataset;
   generating an updated lower energy dataset comprising a combination of the lower energy dataset and the pseudo projection dataset; and
   generating an image from the higher energy dataset and the updated lower energy dataset.

2. The method of claim 1, wherein generating the pseudo projection dataset from the higher energy dataset comprises:
   reconstructing an intermediate image from the higher energy dataset;
   characterizing a high-density material in the intermediate image;
   generating a forward projection dataset based on the high-density material in the intermediate image; and
   combining the forward projection dataset and the higher energy dataset into the pseudo projection dataset.

3. The method of claim 2, wherein generating the pseudo projection dataset from the higher energy dataset further comprises reconstructing a second intermediate image from the lower energy dataset, and wherein generating the forward projection dataset is further based on a characterization of the high-density material in the second intermediate image.

4. The method of claim 2, wherein the intermediate image is reconstructed using filtered back projection.

5. The method of claim 1, wherein the pseudo projection dataset is generated directly from the higher energy dataset by scaling the higher energy dataset with a ratio of an attenuation coefficient of a selected material at lower and higher energies.

6. The method of claim 5, wherein the selected material comprises water.

7. The method of claim 1, wherein the combination of the lower energy dataset and the pseudo projection dataset comprises a weighted sum of the lower energy dataset and the pseudo projection dataset.

8. The method of claim 1, wherein the lower energy dataset and the pseudo projection dataset are combined using a regularization-based iterative optimization.

9. The method of claim 1, wherein generating the image from the higher energy dataset and the updated lower energy dataset comprises:
   decomposing the higher energy dataset and the updated lower energy dataset into material basis datasets;

transforming the material basis datasets into corresponding material density images; and summing the material density images to produce the image.

10. A method for dual energy imaging, comprising:

acquiring a higher energy dataset and a lower energy dataset;

generating a pseudo projection dataset directly from the higher energy dataset;

generating an updated lower energy dataset based on a weighted combination of the lower energy dataset and the pseudo projection dataset; and generating an image based on the higher energy dataset and the updated lower energy dataset.

11. The method of claim 10, wherein generating the pseudo projection dataset directly from the higher energy dataset comprises scaling the higher energy dataset with a ratio of an attenuation coefficient of a selected material at lower and higher energies.

12. The method of claim 10, wherein the weighted combination applies a larger weight to the pseudo projection dataset when a high-density material is in a projection ray.

13. The method of claim 10, wherein generating the image comprises:

decomposing the higher energy dataset and the updated lower energy dataset into material basis datasets;

transforming the material basis datasets into material density images;

summing the material density images; and outputting the summed material density images to a display.

14. The method of claim 13, wherein material bases of the material basis datasets comprise iodine and water.

15. An imaging system, comprising:

an x-ray source that emits a beam of x-rays toward an object to be imaged, the x-ray source configured to emit x-rays with a high energy and a low energy;

a detector that receives the x-rays attenuated by the object;

a data acquisition system (DAS) operably connected to the detector; and a computer operably connected to the DAS and programmed with instructions in non-transitory memory that when executed cause the computer to:

generate pseudo projection data based on higher energy data received from the DAS;

combine the pseudo projection data with lower energy data received from the DAS; and generate an image based on the higher energy data and the combined data.

16. The system of claim 15, wherein the computer is further programmed with instructions in non-transitory memory that when executed cause the computer to:

decompose the combined data and the higher energy data into material basis datasets; and transform the material basis datasets into material density images.

17. The system of claim 16, wherein generating the image comprises summing the material density images.

18. The system of claim 15, wherein the detector and the x-ray source are configured to acquire data in a sparse view mode.

19. The system of claim 15, wherein the x-ray source is configured to switch between a high peak kilovoltage and a low peak kilovoltage to generate respectively the higher energy data and lower energy data.

* * * * *